United States Patent [19]
Outlaw et al.

[11] Patent Number: 4,757,147
[45] Date of Patent: Jul. 12, 1988

[54] PREPARATION OF DIAMINES FROM ALDEHYDES AND AMMONIA

[75] Inventors: Benjamin T. Outlaw, Webster Groves; Bernardus A. Oude Alink, St. Louis, both of Mo.

[73] Assignee: Petrolite Corporation, St. Louis, Mo.

[21] Appl. No.: 772,972

[22] Filed: Sep. 5, 1985

Related U.S. Application Data

[63] Continuation-in-part of Ser. No. 627,947, Jul. 5, 1984, abandoned, which is a continuation-in-part of Ser. No. 193,230, Oct. 2, 1980, abandoned.

[51] Int. Cl.$^4$ .................. C07D 211/02; C07D 211/72
[52] U.S. Cl. .................................. 546/249; 546/304; 546/311
[58] Field of Search ...................... 546/249, 304, 311; 564/509

[56] References Cited

U.S. PATENT DOCUMENTS 3,483,256 12/1969 Delavarenne et al. ......... 564/509 X
3,655,690 4/1972 Hobbs et al. .................... 564/509 X

*Primary Examiner*—Joseph Paul Brust
*Attorney, Agent, or Firm*—S. B. Ring

[57] ABSTRACT

This invention relates to novel highly branched amines and to a process of preparing same which comprises:
  (1) the preparation of a vinylimine from branched aldehydes and ammonia;
  (2) the dimerization and intermolecular condensation of such vinylimines to cyclic diamines; and
  (3) hydrolysis of such cyclic diamines to other diamines.

7 Claims, No Drawings

PREPARATION OF DIAMINES FROM ALDEHYDES AND AMMONIA

This application is a continuation-in-part of application Ser. No. 627,947, filed July 5, 1984, now abandoned, which is a continuation-in-part of application Ser. No. 193,230, filed Oct. 2, 1980, now abandoned.

It is desirable to be able to prepare highly branched amines from inexpensive raw materials.

In accordance with the present invention, there have now been discovered novel highly branched amines and a process of preparing such highly branched amines from inexpensive raw materials by a process which comprises (1) the preparation of vinylimines from branched aldehydes and ammonia;

(2) the dimerization and intramolecular condensation of such vinylimines to afford cyclic diamines; and (3) hydrolysis of such cyclic diamines to afford other diamines.

The novel compounds of the invention are represented by the formulas

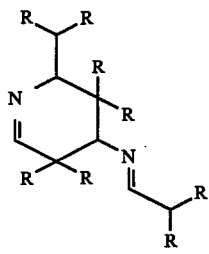

V and

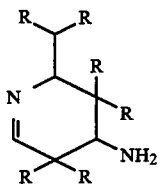

VI wherein each R individually or adjacent Rs together represents hydrogen, alkyl, cycloalkyl, alkenyl, alkinyl, aryl, aralkyl, alkaryl or heterocyclyl groups, e.g. branched or unbranched alkyl groups containing from 1 to about 30 carbon atoms or more, for example, methyl, ethyl, propyl, butyl, amyl, hexyl, heptyl, octyl, nonyl, decyl, dodecyl, tetradecyl, hexadecyl, octadecyl, eicosyl, pentacosyl, triacontyl and the like, preferably, hydrogen, methyl, ethyl, propyl and hexyl, and which may be substituted; cycloalkyl groups containing from 3 to 8 carbon atoms, for example, cyclopropyl, cyclobutyl, cyclopentyl, cyclohexyl, cycloheptyl, cyclooctyl and the like and which may be substituted; branched or unbranched alkenyl group containing from 1 to about 30 carbon atoms or more, for example, ethenyl, propenyl, butenyl, pentenyl, hexenyl, heptenyl, octenyl, nonenyl, decenyl, dodecenyl, pentadecenyl, eicosenyl, triacontenyl, butadienyl, allyl and the like and which may be substituted; branched or unbranched alkinyl groups containing from 1 to about 30 carbon atoms or more, for example, ethinyl, propinyl, butinyl, pentinyl, hexinyl, heptinyl, octinyl, noninyl, decinyl, dodecinyl, pentadecinyl, eicosinyl, triacontinyl and the like and which may be substituted; aryl groups whether singly or in fused ring systems, for example, phenyl, biphenyl, naphthyl and the like and which may be substituted; aralkyl groups, for example, benzylphenylethyl, phenylhexyl, phenyloctyl, phenyldodecyl, naphthyldecyl, phenylheptyl and the like and which may be substituted; alkaryl groups, for example, methylphenyl, propylphenyl, and the like and which may be substituted; heterocyclyl groups, for example furanyl, pyrryl, isoxazolyl, oxazolyl, thiazolinyl, thiazolidinyl, pyrazolyl, imidazolyl, pyranyl, pyridinyl, oxazinyl, diazinyl and the like and which may be substituted; and the like.

Wherein it is indicated that the above-described organic groups may be substituted, it is contemplated that the substituents may be hydrocarbyl, e.g. alkyl, cycloalkyl, alkenyl, alkinyl, aryl, aralkyl, alkaryl, or may be heterocyclyl as described above in detail or may be —OR, wherein R may be H or a hydrocarbyl or heterocyclyl group; hydroxyalkyl;

wherein R may be H or a hydrocarbyl group or heterocyclyl group; amino; amido, e.g., acetamido, benzamido, sulfonamido, benzenesulfonamido, phosphonamido; cyano; cyanate; nitro; nitroso; thiol; benzenesulfonyl; phospho; phosphono and the like.

The compounds of the invention are prepared by a novel process which comprises:

(1) Reaction of α-branched aldehydes (I) with ammonia to afford the corresponding diimines (II) which, upon heating, lose ammonia to afford vinylamines (III) in the manner of Hasek et al, J. Org. Chem. 26, 1822 (1961):

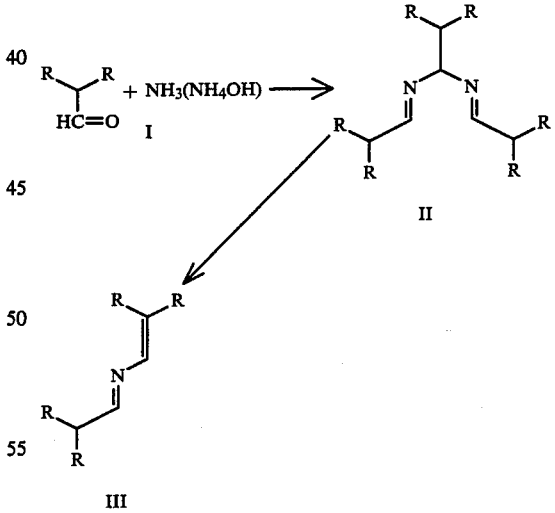

(2) Dimerization and intramolecular condensation of the vinylamines (III) in the presence of a catalytically effective amount of a Lewis acid to afford cyclic diamines (V). The dimerization of the vinylimine (III) is accomplished by a double aldol type condensation which may proceed first through an intermediate via an intermolecular aldol type condensation to an imine (IV) followed by an intramolecular aldol type condensation to the cyclic diamine (V). The intermediate does not have to be isolated:

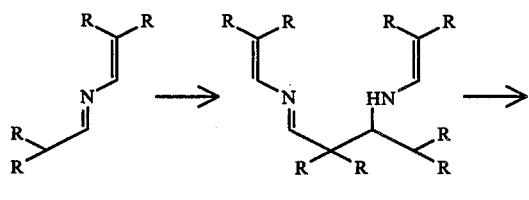

III

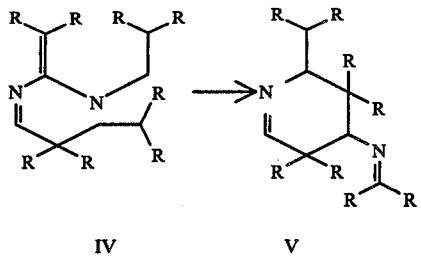

IV     V

The diamine (V) consists of a mixture of stereo-isomeric products.

The acid catalyst may be any Lewis acid, i.e., HCl, NH$_4$Cl, NH$_4$NO$_3$, AlCl$_3$, p-toluene sulfonic acid, and the like. The amount of catalyst used is not critical but must be sufficient to be catalytically effective.

(3) The mixture of diamines (V) upon hydrolysis affords a mixture of other diamines (VI):

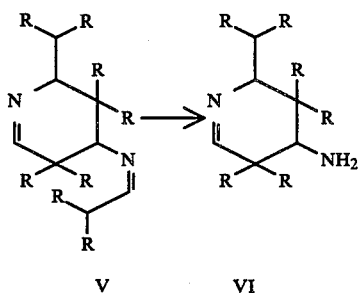

V     VI

The compounds of this invention have a wide variety of uses. For example, they can be used as corrosion inhibitors, biocides, fuel additives, and as intermediates in organic syntheses. They are especially useful as corrosion inhibitors in non-oxygenated aqueous systems containing carbon dioxide.

Representative α-branched aldehydes useful in preparing the compounds of the invention include isobutyraldehyde, α-ethyl butyraldehyde, α-methyl butyraldehyde, α-propylhexanal, α-ethylhexenal and the like.

In general, the aldehyde and ammonia are reacted at ambient temperature and pressure for about 15 to about 25 hours. The diimines (II) thus afforded are then heated at about 150° C. for about 10 to about 20 hours to afford the vinylamines (III) in accordance with the aforedescribed known procedure.

The dimerization of the vinylamines (III) to the cyclic diamine (V) via the intermediate imine (IV) is conducted in the presence of the aforementioned Lewis acid at a temperature of from about 150° C. to about 200° C., preferably about 140° C. to about 170° C.

Hydrolysis of the diamines (V) is conducted at ambient conditions in the presenc of any known hydrolyzing agent, e.g. aqeuous NaOH, HCl and the like.

The following examples are presented for purposes of illustration and not of limitation.

EXAMPLE 1

Preparation of the vinylimine 2,6-Dimethyl-4-azahepta-2,4-diene (III. R=CH$_3$)

To 1400 g of a 28% solution of NH$_4$OH was added, over a period of 4 hours, 1400 g of i-butyraldehyde, temp 22°–47° C. The mixture was stirred for 18 hours at ambient temp. The resulting organic layer (II. R=CH$_3$) was refluxed under azeotropic conditions until NH$_3$ evolution ceased (14 hours). The resulting product was identified as III m/e-125, $^{13}$C nmr (CDCl$_3$), ref. TMS.

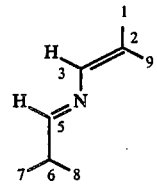

22.5(1), 132.2(2), 137.3(3), 166.0(5), 34.0(6), 19.5(7,8), 17.7(9)

Inasmuch as the R group has no effect on the reaction, it is contemplated that substitution of the methyl group by other alkyl, cycloalkyl, alkenyl, alkinyl, aryl, aralkyl, alkaryl or heterocyclyl groups would afford the corresponding product.

EXAMPLE 2

Dimerization of the vinylimine followed by Intramolecular Aldol type condensation to cyclic diamine 4-(3-Methyl-1-azabutenyl)-6-(1-methylethyl)-3,4,5,6-tetrahydro-3,3,5,5-tetramethyl pyridine (V. R=CH$_3$)

A mixture of 100 g 2,6-dimethyl-4-azahepta-2,4-diene (III) and 1.2 g of p-toluene sulfonic acid was heated at 160° C. for 113 hrs. Ninety seven grams of the crude product was distilled under diminished pressure. The fraction b$_{0.03}$79°–80° (44.3 g) was identified as V. (R=CH$_3$). Two products in GC (45:55), both have m/e=250. $^{13}$C nmr (solvent CDCl$_3$ ref. TMS).

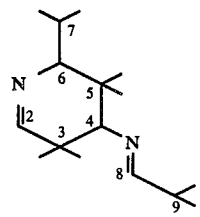

169.1, 168.3(2); 36.36, 36.45(3); 78.4, 82.1(4); 37.5, 38.4(5); 71.3(6); 168.0(8); 33.9(9).

| Analysis | % C | % H | % N |
|---|---|---|---|
| Calc. for C$_{16}$H$_{30}$N$_2$ | 76.74 | 12.08 | 11.19 |
| Found | 75.12 | 12.28 | 11.72 |

Inasmuch as the R group has no effect on the reaction, it is contemplated that substitution of the methyl group by other alkyl, cycloalkyl, alkenyl, alkinyl, aryl, aralkyl, alkaryl or heterocyclyl groups would afford the corresponding product.

EXAMPLE 3

Hydrolysis to another Diamine 4-amino-6-(methylethyl)-3,4,5,6-tetrahydro-3,3,5,5-tetramethyl pyridine (VI. R=CH₃)

A mixture of 5 g of distilled V and 25 ml 5N HCl was refluxed for 25 hrs. The reaction mixture was extracted with ether. The acidic aqueous fraction was basified with 20% NaOH which was then extracted with ether. The ether extract was evaporated to yield 3.1 g of VI. Two products in GC/MS (45:55), both m/e=196. $^{13}$C nmr (solvent CDCl₃), ref. TMS.

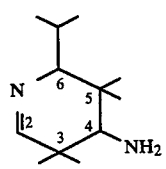

168.2(2); 57.5, 63.1(4); 71.9, 73.6(6).

Inasmuch as the R group has no effect on the reaction, it is contemplated that substitution of the methyl group by other alkyl, cycloalkyl, alkenyl, alkinyl, aryl, aralkyl, alkaryl or heterocyclyl groups would afford the corresponding product.

EXAMPLE 4

A corrosion sparge test was run to determine corrosion inhibitory efficiency of the compounds of the invention.

The compound of Example 2 was added (50 ppm) to a 6% aqueous solution of laboratory brine formulated to simulate oil field brine. Mild steel coupons were submersed in the control and test brines. The brines were stirred by magnetic stirrer and CO₂ was sparged into the brines over a 24 hour period at ambient temperature. At the end of the test period, the control coupon had corroded at the rate of 104 mils per year (mpy), whereas the coupon protected with the compound of Example 2 had corroded only at the rate of 56 mpy, approximately a 100 percent improvement over the control in the corrosion rate.

The compounds of the invention may be formulated with other materials normally used in the treatment of aqueous systems, e.g. biocides, scale inhibitors, other corrosion inhibitors, emulsifiers, demulsifiers, water clarifying agents and the like.

We claim:

1. A composition of the formula

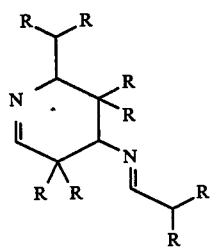

wherein R represents alkyl.

2. A composition of the formula

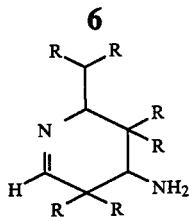

wherein R represents alkyl.

3. A composition having the formula

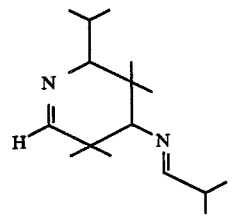

4. A composition having the formula

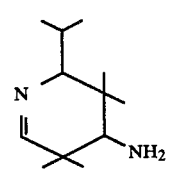

5. Process of preparing the composition of claim 1 which comprise heating, dimerizing and condensing a compound of the formula

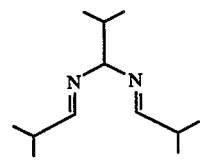

in the presence of a Lewis acid at a temperature of from about 150° to about 200° C.

6. Process of preparing the composition of claim 1 which comprises dimerizing and condensing a compound of the formula

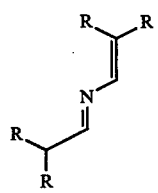

wherein R represents alkyl in the presence of a Lewis acid at a temperature of from about 150° to about 200° C.

7. Process of preparing the composition of claim 2 which comprises hyrolyzing a composition of the formula

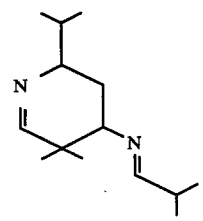

* * * * *

UNITED STATES PATENT AND TRADEMARK OFFICE
CERTIFICATE OF CORRECTION

PATENT NO. : 4,757,147
DATED : July 12, 1988
INVENTOR(S) : Benjamin T. Outlaw and Bernardus A. Oude Alink It is certified that error appears in the above-identified patent and that said Letters Patent is hereby corrected as shown below:

At Column 3, lines 10-20; delete Figure IV and substitute therefor:

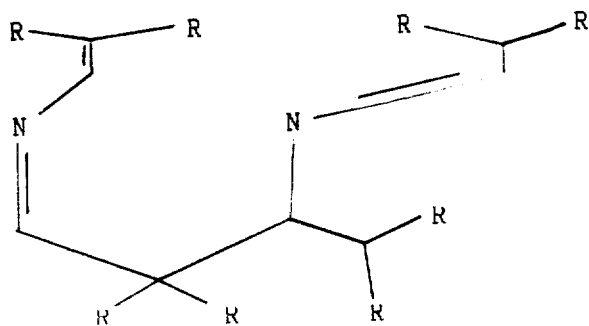

Signed and Sealed this

Thirteenth Day of December, 1988

Attest:

DONALD J. QUIGG

Attesting Officer

Commissioner of Patents and Trademarks